(12) United States Patent
Erdem et al.

(10) Patent No.: US 10,071,870 B2
(45) Date of Patent: Sep. 11, 2018

(54) METHODS OF WINDING SUBSTRATES HAVING THREE-DIMENSIONAL FEATURES

(71) Applicant: The Procter & Gamble Company, Cincinnati, OH (US)

(72) Inventors: Gueltekin Erdem, Bad Soden (DE); Nadezhda Kurbatova, Schwalbach Am Taunus (DE); Joseph Hung Lam, Mason, OH (US); Sudhanshu Gupta, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 300 days.

(21) Appl. No.: 15/071,553

(22) Filed: Mar. 16, 2016

(65) Prior Publication Data
US 2016/0280503 A1 Sep. 29, 2016

Related U.S. Application Data

(60) Provisional application No. 62/138,426, filed on Mar. 26, 2015.

(51) Int. Cl.
*B65H 18/10* (2006.01)
*B65H 18/28* (2006.01)
*A61F 13/15* (2006.01)

(52) U.S. Cl.
CPC ....... *B65H 18/10* (2013.01); *A61F 13/15747* (2013.01); *A61F 13/15764* (2013.01);
(Continued)

(58) Field of Classification Search
CPC .... B65H 18/28; B65H 18/08; B65H 2801/57; B65H 2301/412845; A61F 13/15747; A61F 13/15764; A61F 13/51104
See application file for complete search history.

(56) References Cited

U.S. PATENT DOCUMENTS

| 2,717,037 A | 9/1955 | Goodwillie et al. |
| 3,025,015 A * | 3/1962 | Mix ........................ B65H 75/02 |
| | | 242/613.2 |

(Continued)

FOREIGN PATENT DOCUMENTS

| GB | 2350375 | 11/2000 |
| JP | S63300058 | 12/1988 |

(Continued)

OTHER PUBLICATIONS

EP Search Report, EP Application No. EP15161010.
(Continued)

*Primary Examiner* — William E Dondero
(74) *Attorney, Agent, or Firm* — Christian M. Best

(57) ABSTRACT

The present disclosure provides methods of winding substrates comprising three-dimensional features about a core to form a spool so that at least a majority of the three-dimensional features in one wrap of a lane of the spool are at least partially nested with a majority of the three-dimensional features in another adjacent wrap in the same lane of the spool. By at least partially nesting these three-dimensional features in adjacent wraps of a lane of the spool, the three-dimensional features may be at least mostly maintained in the substrates without significant compression during winding and storage of the spool.

23 Claims, 11 Drawing Sheets

(52) U.S. Cl.
CPC . *B65H 18/28* (2013.01); *B65H 2301/412845* (2013.01); *B65H 2701/18444* (2013.01); *B65H 2801/57* (2013.01)

(56) References Cited

U.S. PATENT DOCUMENTS

| | | |
|---|---|---|
| 3,549,099 A | 12/1970 | Hofbauer et al. |
| 4,024,696 A | 5/1977 | Townsend |
| 4,267,985 A | 5/1981 | Rogers |
| 4,634,070 A | 1/1987 | Looper |
| 6,007,016 A | 12/1999 | Helton |
| 6,138,934 A | 10/2000 | Helton |
| 6,209,814 B1 | 4/2001 | Helton |
| 6,533,213 B2 | 3/2003 | Durrance et al. |
| 8,157,197 B2 | 4/2012 | Jelinek et al. |
| 9,932,186 B2 | 4/2018 | Erdem et al. |
| 2003/0047632 A1 | 3/2003 | Duncan |
| 2003/0122009 A1 | 7/2003 | Abba et al. |
| 2013/0135728 A1 | 5/2013 | Hirata et al. |
| 2016/0280490 A1 | 9/2016 | Erdem et al. |

FOREIGN PATENT DOCUMENTS

| | | |
|---|---|---|
| JP | H11208954 | 8/1999 |
| JP | 2005287725 | 10/2005 |

OTHER PUBLICATIONS

International Search Report and Written Opinion, PCT/US2016/022528, dated Jun. 10, 2016.
All Office Actions for U.S. Appl. No. 15/071,516.
All Office Actions for U.S. Appl. No. 15/071,532.

* cited by examiner

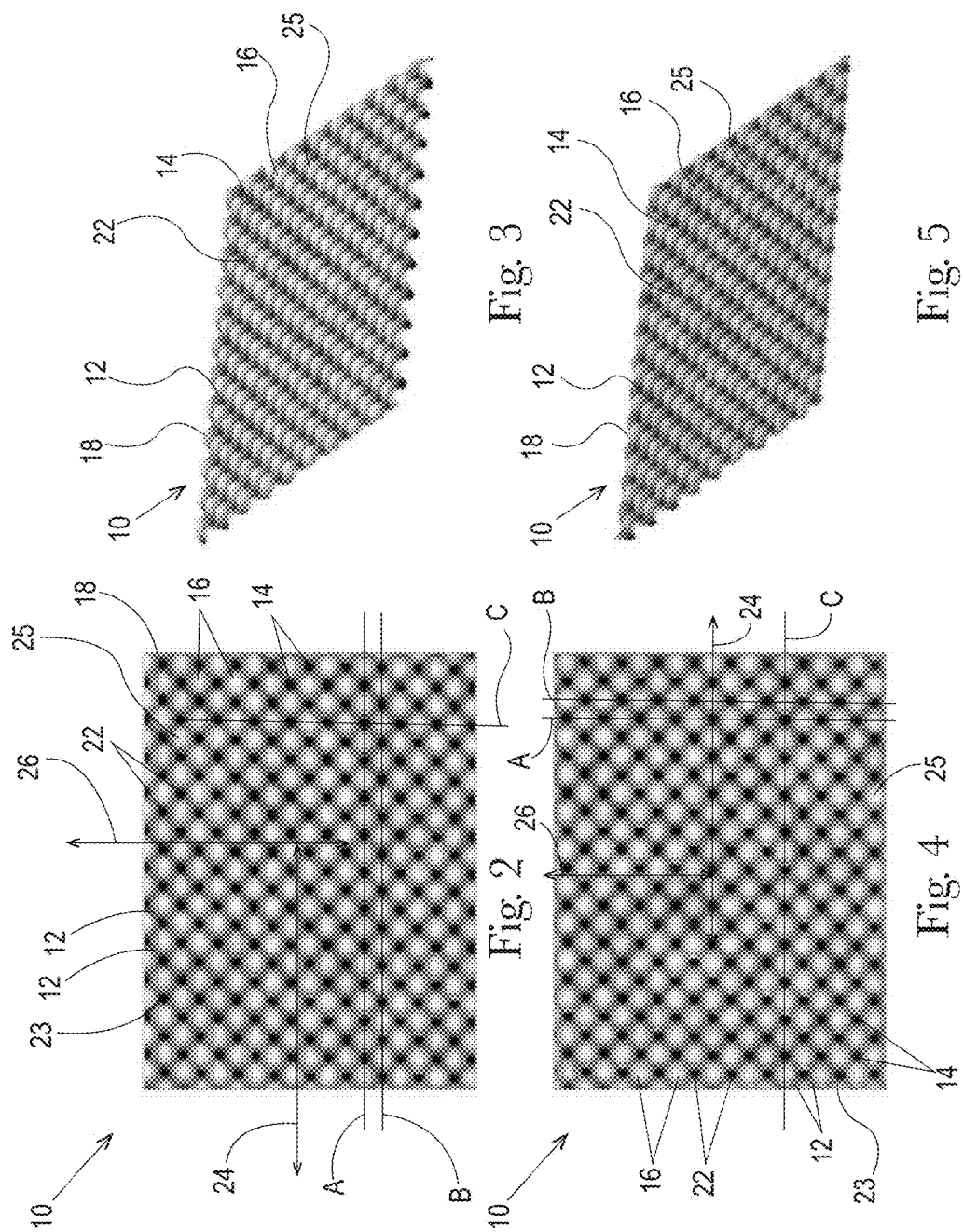

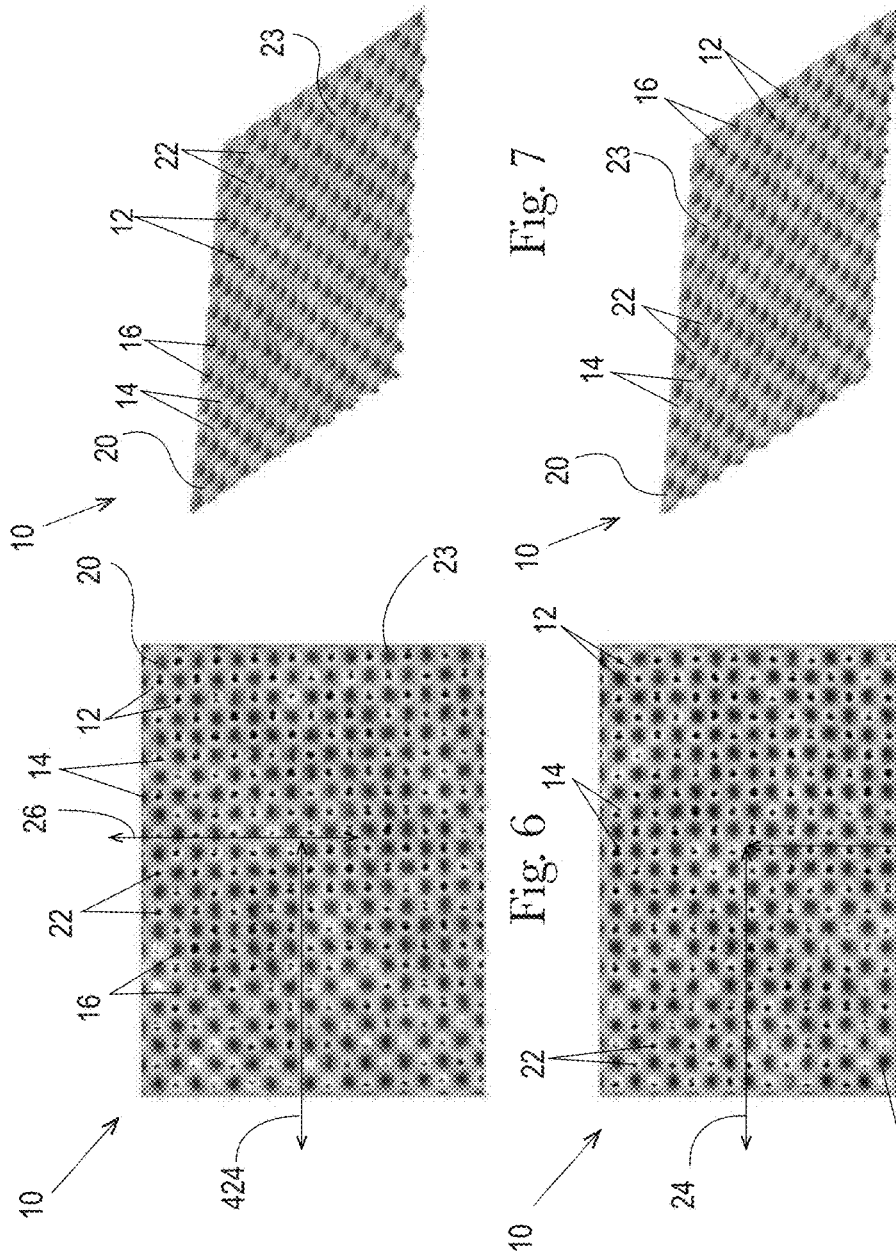

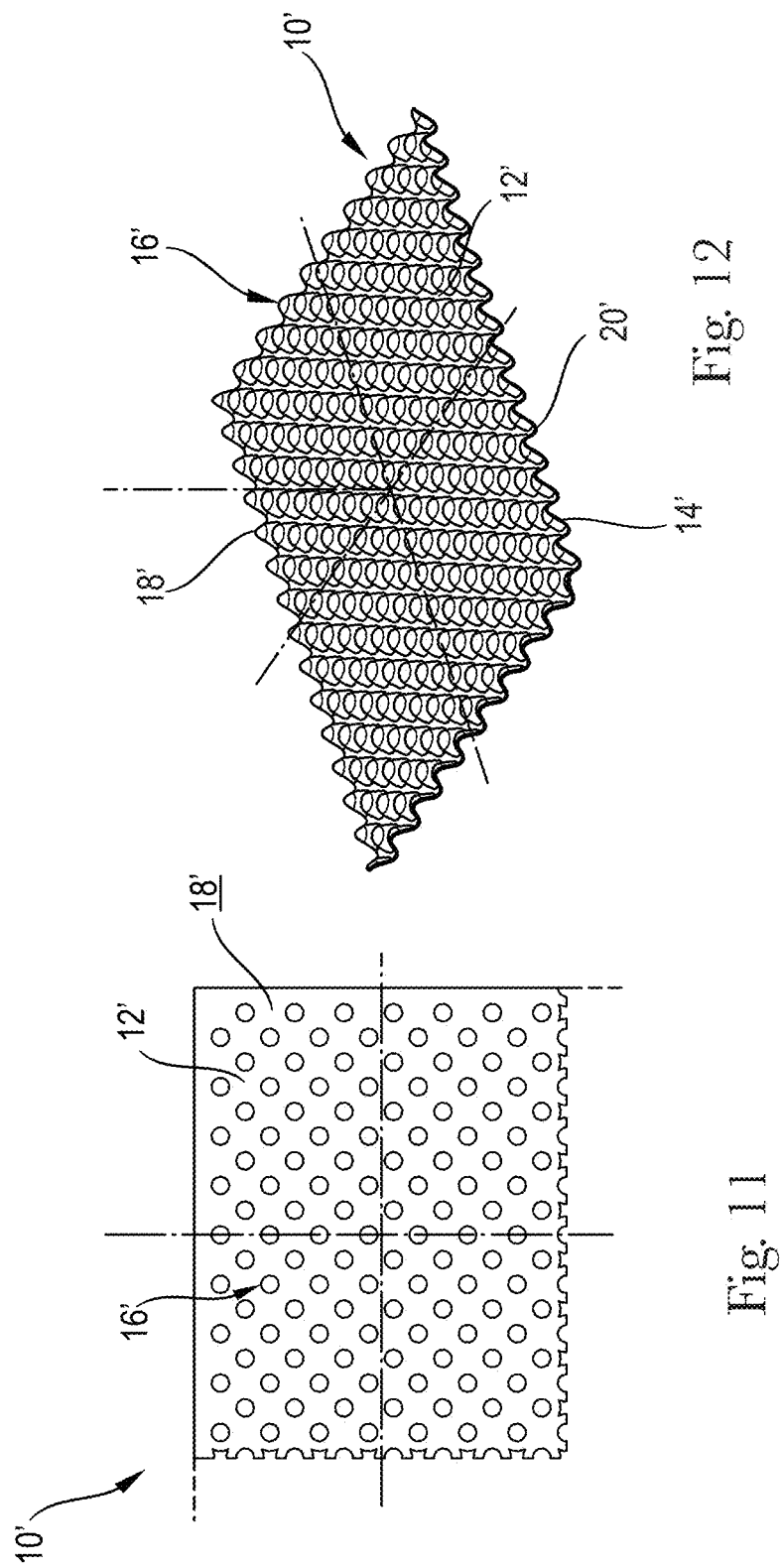

METHODS OF WINDING SUBSTRATES HAVING THREE-DIMENSIONAL FEATURES

CROSS REFERENCE TO RELATED APPLICATIONS

This application claims the benefit, under 35 U.S.C. § 119(e), to U.S. Provisional Patent Application No. 62/138,426, filed on Mar. 26, 2015, which is hereby incorporated by reference in its entirety.

FIELD

The present disclosure relates to methods of winding substrates having a plurality of three-dimensional features onto a spool.

BACKGROUND

Absorbent articles for personal hygiene, such as disposable diapers, training pants, adult incontinence undergarments, and/or sanitary napkins are designed to absorb and contain bodily exudates, in particular large quantities of urine, runny BM, and/or menses. These absorbent articles may typically comprise several layers providing different functions, for example, a topsheet, a backsheet, one or more acquisition/distribution layers, and an absorbent core disposed between the topsheet and the backsheet.

Substrates, such as nonwoven substrates or laminates comprising nonwoven substrates, have been provided as topsheets, outer covers, acquisition/distribution layers, and/or other portions of absorbent articles. The substrates may comprise a plurality of three-dimensional features, such as a plurality of projections and a plurality of recesses, for example.

Substrates comprising three-dimensional features may also be useful in other areas, such as in the areas of cleaning wipes, dusting wipes, filtration media, and/or any other suitable areas.

Typical, substrates comprising a plurality of three-dimensional features are wound on a core and stored in the form of a spool. The spool can then be unwound and converted for use in making any suitable products, such as components of absorbent articles, wipes, cleaning items, and/or filtration media. Generally, the substrates comprising a plurality of three-dimensional features are helically wound around a core from a first end of the core to a second end of the core and then from the second end to the first end (sometimes many times) to form a plurality of helically wound wraps of the substrate around the core and in the spool. Owing to the helical winding of the wraps and the pressure exerted on some of the inner wraps, the three-dimensional features of the substrates may not be properly preserved during winding and storage. The helical winding of the wraps of the substrates results in non-nesting or limited nesting of the three-dimensional features in adjacent wraps of the substrates. This non-nesting or limited nesting can result in three-dimensional features in that substrate that are at least partially collapsed or compressed when unwound from the spool. The at least partially collapsed or compressed three-dimensional features may not be consumer preferred for performance and/or aesthetic reasons. What is needed are methods of winding substrates comprising three-dimensional features that provide for at least partial nesting (between the various adjacent wraps) of at least a majority of the three-dimensional features of the substrates to provide more aesthetically pleasing and/or better performing substrates having three-dimensional features that are not overly compressed or collapsed.

SUMMARY

The present disclosure provides methods of winding substrates comprising three-dimensional features. The methods increase the nesting, or at least partial nesting, of the three-dimensional features of the substrates with themselves in adjacent wraps to allow the substrates to maintain their structure during winding and while on the spool. The increase in nesting is accomplished by spirally winding a majority of the spools (e.g., greater than 50%) into lanes and having very few helically wound portions intermediate the spirally wound lanes. Machine direction tension may be applied to the substrates comprising the three-dimensional features during winding. This machine direction tensioning has been found to aid nesting, or at least partial nesting, of the three-dimensional features of the substrates. Indeed, a relatively low machine direction tension applied to the substrates comprising the three-dimensional features may help to stretch the three-dimensional features without any, or very little, irreversible deformations. Being slightly stretched in the machine direction, the three-dimensional features of adjacent overlaying layers of the substrate have been found to have the tendency to slightly shift and rearrange in order to coincide and at least partially, or fully, nest together. Having at least partially, or fully, nested three-dimensional features may help the substrates reach a more stable state (i.e., a lower energy state) on the spool and help the three-dimensional features maintain their structure during winding and while on the spool.

A nip roll may also be used to aid in nesting, or at least partial nesting, of one layer of the substrate comprising three-dimensional features with another adjacent layer of the substrate comprising three-dimensional features. The nip roll may apply a force to the substrate in a direction generally toward a core of a spool to cause the three-dimensional features in various layers of the substrate to at least partially, or fully, nest with each other.

In a form, an example method of winding a substrate comprising a nonwoven on a core to create a spool of the substrate is provided. The substrate comprises a plurality of three-dimensional features. The core defines a longitudinal axis and has a first end and second end. The method comprises spirally winding a plurality of wraps of the substrate about the core to at least partially form a first lane. A majority of the three-dimensional features in at least some of the wraps of the first lane are at least partially nested with a majority of the three-dimensional features in an adjacent wrap in the first lane. The method comprises helically winding at least a ⅕ wrap to at most 2 wraps of the nonwoven substrate about the core to transition to a second lane, and spirally winding a plurality of wraps of the nonwoven substrate about the core to at least partially form the second lane. A majority of the three-dimensional features in at least some of the wraps of the second lane are at least partially nested with a majority of the three-dimensional features in an adjacent wrap of the second lane. The method comprises helically winding at least a ⅕ wrap to at most 2 wraps of the substrate about the core to transition to a third lane and spirally winding a plurality of wraps of the substrate about the core to at least partially form the third lane. A majority of the three-dimensional features in at least some of the wraps of the third lane are at least partially nested with a majority of the three-dimensional features in an adjacent wrap of the third lane. The method comprises applying less than about 10%, less than about 8%, less than about 5%, less than about 3%, less than about 2%, less than about 1.5% MD strain on the substrate during the spirally and helically winding steps.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein:

FIG. 2 is a front view of a portion of a substrate comprising three-dimensional features in accordance with the present disclosure;

FIG. 3 is a front perspective view of the portion of the substrate of FIG. 2 in accordance with the present disclosure;

FIG. 4 is another front view of a portion of a substrate comprising three-dimensional features in accordance with the present disclosure;

FIG. 5 is a front perspective view of the portion of the substrate of FIG. 4 in accordance with the present disclosure;

FIG. 6 is a back view of a portion of the substrate of FIG. 2 in accordance with the present disclosure;

FIG. 7 is a back perspective view of the portion of the substrate of FIG. 2 in accordance with the present disclosure;

FIG. 8 is a back view of a portion of the substrate of FIG. 4 in accordance with the present disclosure;

FIG. 9 is a back perspective view of the portion of the substrate of FIG. 4 in accordance with the present disclosure;

FIG. 11 is a top view of a portion of an example substrate comprising a plurality of three-dimensional features in accordance with the present disclosure;

FIG. 12 is a top perspective view of the portion of the example substrate of FIG. 11 in accordance with the present disclosure;

DETAILED DESCRIPTION

Figure 1:
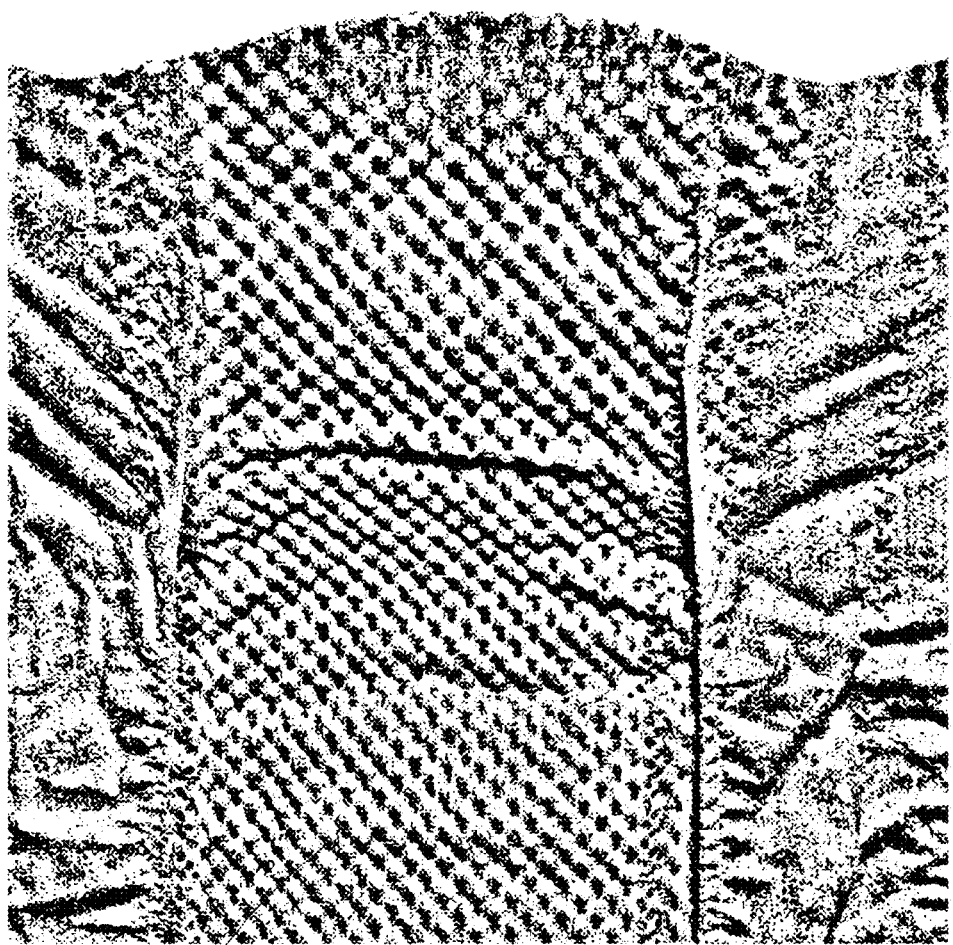
FIG. 1 is a top view of a portion of a substrate comprising three-dimensional features used as a topsheet of an absorbent article.
Figure 10:
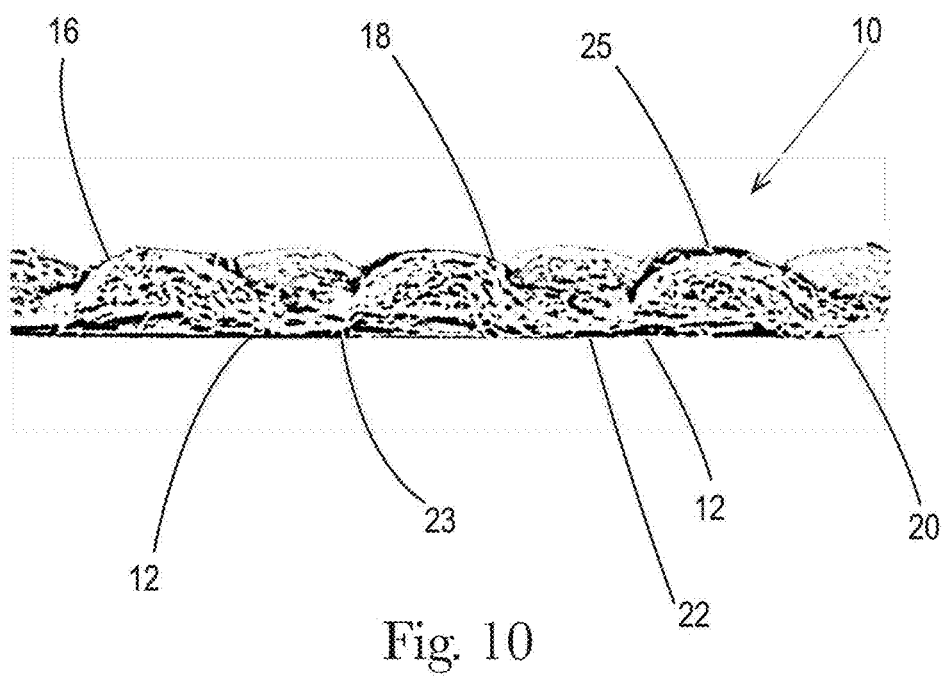
FIG. 10 is a cross-sectional view of a substrate comprising three-dimensional features in accordance with the present disclosure.

Various non-limiting forms of the present disclosure will now be described to provide an overall understanding of the principles of the structure, function, manufacture, and use of the methods of winding substrates having three-dimensional features disclosed herein. One or more examples of these non-limiting forms are illustrated in the accompanying drawings. Those of ordinary skill in the art will understand that the methods of winding substrates having three-dimensional features disclosed herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Definitions

The term "absorbent article", as used herein, refers to devices which absorb and contain body exudates, and, more specifically, refers to devices which are placed against or in proximity to the body of the wearer to absorb and contain the various bodily exudates discharged from the body. Typical absorbent articles include but are not limited to diapers, adult incontinence briefs, training pants, sanitary napkins, and panty liners. Absorbent articles also include wipes, such as household cleaning substrates, scrubbing substrates, dusting substrates, wet and dry wipes, and/or baby wipes.

The term "machine direction", as used herein, means the direction that is generally parallel to the flow of a substrate through a process.

The term "cross-machine direction", as used herein, means a direction that is generally perpendicular to the machine direction.

The term "nonwoven" or "nonwoven substrate", as used herein, means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven substrates may be formed by many processes such as meltblowing, spunbonding, solvent spinning, electrospinning, carding, and airlaying.

The term "three-dimensional features" contemplates areas of a substrate having different heights (more than a typical generally planar nonwoven substrate). Projections and recesses in a substrate are just one example of three-dimensional features. Ridges and valleys running in the machine direction, in the cross-machine direction, or other direction are also contemplated as three-dimensional features. The three-dimensional features may be formed by any suitable process such as embossing, for example.

Substrates Comprising Three-Dimensional Features

The methods of the present disclosure are useful in winding substrates comprising a plurality of three-dimensional features. An example substrate 1 comprising three-dimensional features and used as a topsheet of an absorbent article is illustrated in FIG. 1. The substrates of the present disclosure may comprise nonwovens, may comprise laminates of nonwovens and other materials, such as films and cellulosic materials, may not comprise nonwovens, or may comprise any suitable materials. The three-dimensional features may comprise a plurality of projections and/or a plurality of recesses or may comprise any other suitable three-dimensional features. In some instances, the three-dimensional features may comprise a plurality of projections extending from a first side of a substrate and that form a plurality of hollow recesses on a second side of the substrate. The three-dimensional features may also comprise a plurality of second recesses formed on the first side of the substrate forming a plurality of second projections on the second side of the substrate.

The substrates useful with the present methods may be useful as components of, or form all of, absorbent articles, cleaning wipes, dusting wipes, other suitable wipes, paper towels, sanitary tissue, mats, filtration media, or any other suitable products, whether final or intermediate products.

Referring generally to FIGS. 2-10, an example substrate 10 comprising a plurality of three-dimensional features may comprise a first layer and a second layer, more than two layers, or one layer. The substrate 10 may comprise a plurality of land areas 12, a plurality of recesses 14, and a plurality of projections 16 on a first side 18 of the substrate 10. The plurality of land areas 12, the plurality of recesses 14, and the plurality of projections 16 may together form three-dimensional features on the first side 18 of the substrate 10. The plurality of land areas 12, the plurality of recesses 14, and the plurality of projections 16 may also form three-dimensional features on a second side 20 of the substrate 10. The projections 16 may be generally dome shaped on the first surface 18 of the substrate 10 and may form arch-shaped hollow recesses on the second side 20 of the substrate 10. The recesses 14 may form second projections on a second side of the substrate 10. All of, or a majority of (i.e., more than 50% of, or more than 75% of), or substantially all of, the recesses 14 may define an aperture 22 therein at a location most distal from a top peak 25 of an adjacent projection 16. A perimeter 23 of a majority of, or all of, the apertures 22 may form a bottommost portion or plane of the substrate 10, while the top peak 25 (i.e., uppermost portion) of a majority of, or all of, the projections 16 may form a topmost portion or plane of the substrate 10. In other instances, the substrate may not have apertures within the recesses 14 and the portion of the recesses 14 most distal from the top peaks 25 of the projections 16 may form the bottommost portion or plane of the substrate 10. The apertures 22 may extend through the first and the second layers (or all of the layers) of the substrate 10, if two or more layers are provided.

The land areas 12 may be positioned intermediate: (1) adjacent projections 16, (2) adjacent recesses 14 and/or adjacent apertures 22. The land areas 12 may also surround at least a portion of, or all of, a majority of, or all of, the recesses 14 and/or the apertures 22 and at least a majority of, or all of, the projections 16. The land areas 12 may be positioned between a plane of a perimeter of at least a majority of the apertures 22 and a plane of at least a majority of the top peaks 25 of the projections 16. The land areas 12, in some instances, may be generally non-three-dimensional.

The projections 16 may alternate with the recesses 14 and/or the apertures 22 in a direction generally parallel with a lateral axis 24 of the substrate 10. The projections 16 may also alternate with the recesses 14 and/or apertures 22 in a direction generally parallel with a longitudinal axis 26 of the substrate 10. In such a configuration, in a direction generally parallel with the lateral axis 24 or in a direction generally parallel with the longitudinal axis 26, the projections 16 and the recesses 14 and/or apertures 22 alternate (i.e., projection, recess and/or apertures, projection, recess and/or aperture). This feature provides better softness to the substrate 10 in that there is a soft projection peak 25 intermediate most of, or all of, adjacent recesses 14 and/or apertures 22. In an absorbent article context, this feature also helps maintain the skin of a wearer away from fluids in the land areas 12 and/or the recesses 14, since the projections 16 essentially create a spacer between the skin and the fluids.

Two or more adjacent projections 16 may be separated from each other by a recess 14 and/or an aperture 22 and one or more land areas 12 in a direction generally parallel to the lateral axis 24 or in a direction generally parallel to the longitudinal axis 26. Two or more adjacent recesses 14 and/or apertures 22 may be separated by a projection 16 and one or more land areas 12 in a direction generally parallel to the lateral axis 24 or in a direction generally parallel to the longitudinal axis 26. The land areas 12 may fully surround the apertures 22 and the projections 16. The land areas 12, in some instances, may together form a generally continuous grid through the substrate 10, while the projections 16 and the recesses 14 and/or the apertures 22 may be discrete elements throughout the substrate 10.

In some instances, two or more, such as four projections 16 may be positioned around at least a majority of, substantially all of, or all of, the recesses 14 and/or the apertures 22 (this does not include the land areas 12 intermediate the projections 16 and the recesses 14 and/or the apertures 22). Two or more recesses 14 and/or apertures 22, such as four, may be positioned around at least a majority of, substantially all of, or all of, the projections 16 (this does not include the land areas 12 intermediate the recesses 14 and/or the apertures 22 and the projections 16). The projections 16, recesses 14, apertures 22, and land areas 12 may all be formed of portions of the first and second layers of the substrate. If more than two layers are provided in a substrate, the projections 16, recesses 14, apertures 22, and land areas 12 may all be formed of portions of the first, second, and third layers of the substrate. The same may be true if more than three layers are provided in a particular substrate.

The apertures 22 and/or the recesses 14 may comprise a first set of apertures and/or recesses 14 together forming a first line in the substrate 10 and a second set of apertures 22 and/or recesses 14 together forming a second line in the substrate 10. The first line may be generally parallel with or generally perpendicular to the second line. The first line may also form an acute or obtuse angle with the second line. The projections 16 may comprise a first set of projections 16 together forming a first line in the substrate 10 and a second set of projections 16 together forming a second line in the substrate 10. The first line may be generally parallel with, or generally perpendicular to, the second line. The first line may also form an acute or obtuse angle with the second line.

The substrate 10 may be generally symmetrical about the lateral axis 24 and/or generally symmetrical about the longitudinal axis 26. In other instances, the substrate may not be symmetrical about the lateral axis 24 and/or the longitudinal axis 26.

In a form, the substrate 10 may comprise a first line comprising alternating apertures 22 and projections 16 extending in a direction parallel to the lateral axis 24 and a second adjacent line comprising alternating apertures 22 and projections 16 extending in the direction generally parallel to the lateral axis 24. The lines will run through the center of the apertures 22 and the projections 16. See for, example, FIG. 2, lines A and B. If a line, C, is drawn in a direction generally parallel to the longitudinal axis 26 and that intersects lines A and B, an aperture 22 will be located at the intersection of lines A and C and a projection 16 will be located at the intersection of the lines B and C. The same is true if lines A and B are drawn in a direction parallel to the longitudinal axis 26 and line C is draw in a direction generally parallel to the lateral axis 24, as illustrated in FIG. 4. If the lines are drawn at different locations, the intersection of lines A and C may have a projection 16 and the intersection of lines B and C may have an aperture 22. The main point being that the rows of apertures and the rows of projections are staggered. By staggering the apertures and projections in this fashion, better softness is achieved in the wearer-facing surface of the substrate 10 owing to a soft projection or projection crest being intermediate two apertures.

Wraps of the example substrate 10 comprising the three-dimensional features, when wound upon a core of a spool, may at least partially nest with other adjacent wraps. This nesting or partial nesting of at least some of the three-dimensional features in the wraps prevents, or at least inhibits, compression of at least some of the three-dimensional features. For example, when a plurality of wraps of the substrate 10 are wound on a core of a spool, the next adjacent wrap may at least partially nest with the outermost existing wrap on the partially wound spool. In such an instance, the first surface 18 of the substrate 10 may be facing outward on the partially wound spool, when a next adjacent wrap of the substrate 10 is wound upon the existing substrate 10 on the spool, the projections 16 may be at least partially covered by the hollow arches or second recesses in the next adjacent wrap formed by the undersign of the projections in that next adjacent wrap. The projections extending from the second surface 20 (formed by the recesses 14) in the next adjacent wrap may at least partially engage the recesses 14 in the existing wrap on the spool. In such an instance, the next adjacent wrap is at least partially "nested" with the outermost existing wrap on the spool.

If the second surface 20 of the substrate 10 is facing outward on the spool, three-dimensional features of the next adjacent wrap may still at least partially nest with the three-dimensional features of the wrap on the spool. For example, the recesses formed by the hollow portions of the projections 16 of the outermost portion of the wrap on the spool may be engaged by the projections 16 in the next adjacent wrap. The projections extending from the second side 20 of the substrate 10 formed by the recesses 14 of the outermost wrap on the spool may be at least partially overlapped by the recesses 14 in the next adjacent wrap. In such an instance, the next adjacent wrap is at least partially "nested" with the existing wrap on the spool.

Figure 13:
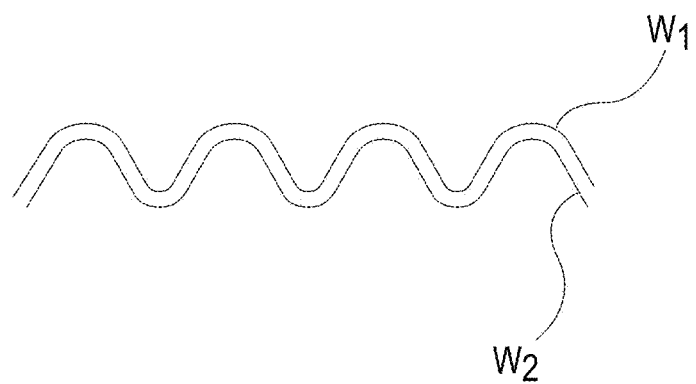
FIG. 13 is a schematic cross-sectional view of two adjacent wraps of a three-dimensional substrate being at least partially nested in accordance with the present disclosure.

Referring to FIGS. 11 and 12, another example substrate 10' comprising a plurality of three-dimensional features is illustrated. The substrate 10' may comprise a plurality of projections 16' (e.g., three-dimensional features) and a plurality of land areas 12' on a first surface 18' and a plurality of recesses 14' (e.g., three-dimensional features) formed by the projections 16' and the plurality of land areas 12' on a second surface 20'. When a certain wrap of the substrate 10' is wound about a core of a spool with the first surface 18' facing outwardly, recesses 14' in a next adjacent wrap may at least partially overlap at least some of the projections 16'. In such an instance, the next adjacent wrap is at least partially "nested" with the outermost wrap on the spool. An example of this nesting, or partial nesting, is illustrated in FIG. 13 with portions of two wraps (W1 and W2) "nested" or at least partially "nested". When a certain wrap of the substrate 10' is wound about the core with the second surface 20' facing outwardly, projections 16' in a next adjacent wrap may at least partially engage the recesses 14'. In such an instance, the next adjacent wrap is at least partially "nested" with the existing wrap on the core of the spool.

Methods of Winding Substrates Having Three-Dimensional Features

Figure 14:
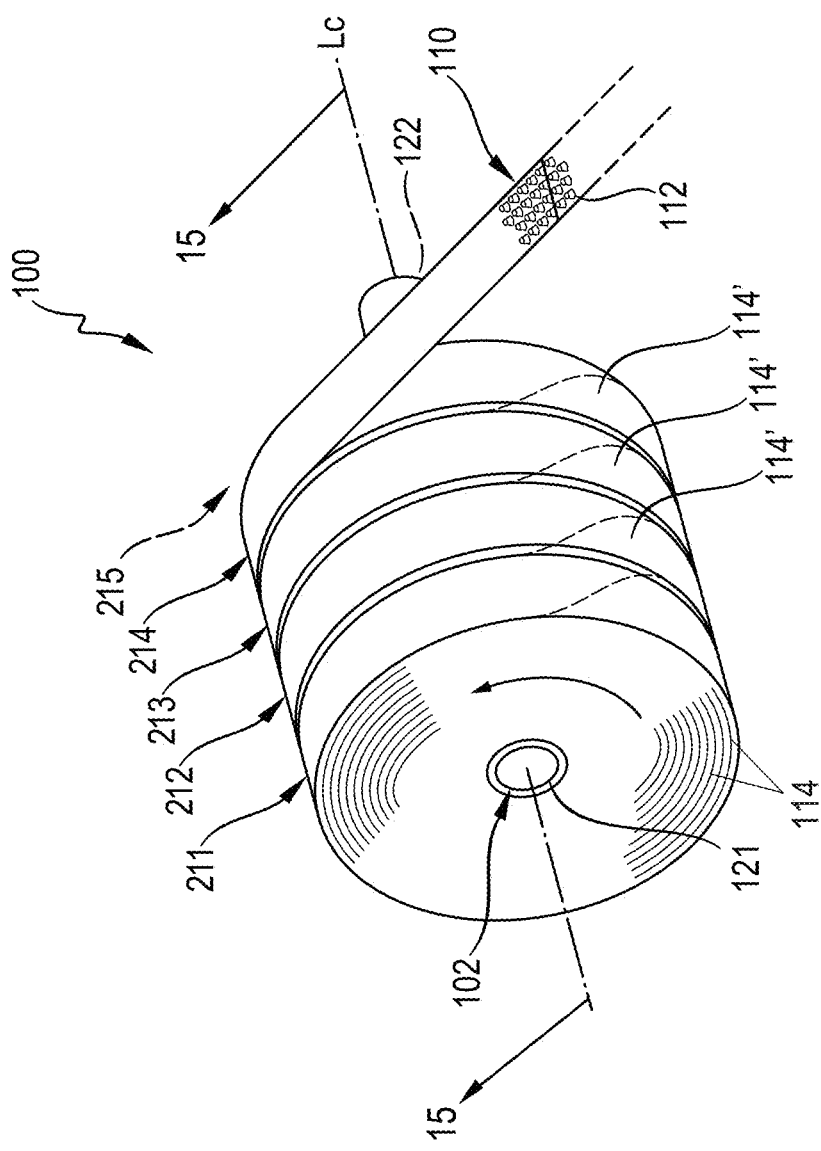
FIG. 14 is a perspective view of a spool being wound in accordance with the methods of the present disclosure.
Figure 15:
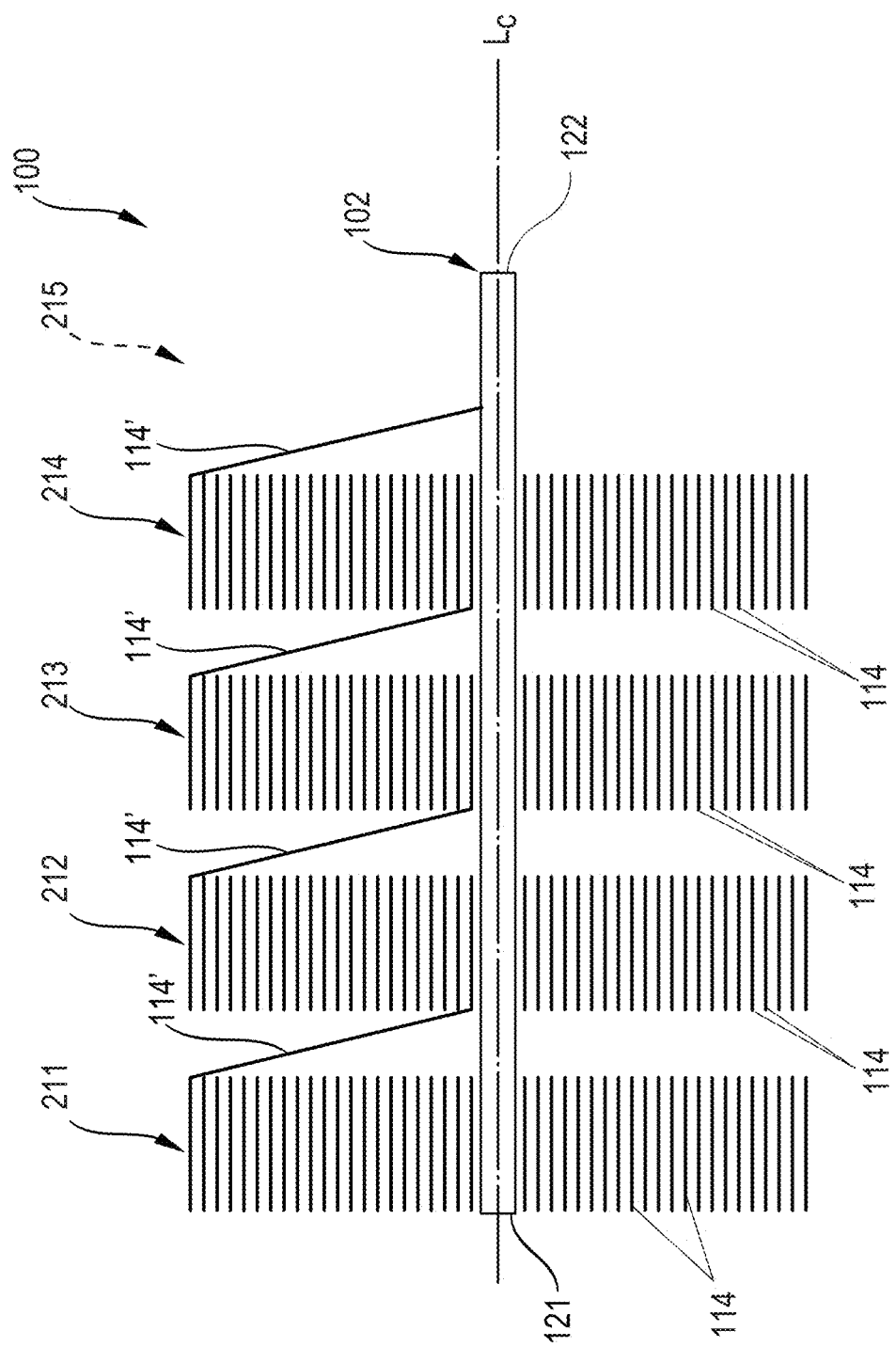
FIG. 15 is a schematic cross-sectional view of the spool taken about line 15-15 of FIG. 14 in accordance with the methods of the present disclosure.

FIGS. 14 and 15 illustrate an example partially wound spool 100 that is being wound by one of the example methods of the present disclosure. The last lane (or fifth lane 215 in this example) of the spool 100 has not yet been wound in FIGS. 14 and 15. The spool 100 comprises a core 102 having a first end 121 and a second end 122. The core 102 may have any suitable diameter such as about 3 inches to about 14 inches, about 4 inches to about 12 inches, or about 8 inches, for example, and may be made by any suitable material(s). The core 102 has a longitudinal axis Lc and is rotated about its longitudinal axis Lc during substrate winding by any suitable device or devices known to those of skill in the art. A substrate 110 having a plurality of three-dimensional features 112 is wrapped around the rotating core 2. Any suitable substrates having a plurality of three-dimensional features, such as the substrates described above, may also be used in the methods of winding of the present disclosure. Mainly, the substrates of interest are substrates having three-dimensional features that will at least partially nest with each other during spiral winding. The substrate may be one or more nonwoven substrates, may comprise one or more nonwoven substrates, or may be a laminate comprising one or more nonwoven substrates and one or more other materials, such as films or cellulosic materials, for example. Each substrate may comprise any suitable number of layers or plys. In a finished spool, the core 102 may extend outwardly in the direction of the longitudinal axis Lc from the wound substrate 100 on either end 121, 122 or the substrate 110 may be wound to the ends 121, 122 of the core 102. The spool 100 may comprise any suitable number of lanes, such as 2 to 15, for example. The number of spirally wound wraps of the substrate 110 on a particular lane in a finished spool may vary depending on the substrate being wound, the desired spool size, and/or the manufacturing process that the spool is being prepared for. A wrap is one full circumferential revolution of the substrate 110 about the core 102 regardless of whether helical wound wraps or spirally wound wraps are being discussed.

Methods of winding a substrate comprising a plurality of three-dimensional features onto a core to create a spool of the substrate are provided. The methods are directed, at least in part, to reducing the amount of transition areas between the various lanes of the spool to provide a spool with a substrate that is better nested and has less compression of the plurality of three-dimensional features. The transition areas are equated to the helically wound portions.

Referring again to FIGS. 14 and 15, the spool 100 may be fully wound from the first end 121 to the second end 122 or fully wound from the second end 122 to the first end 121. By only winding in one direction on the core 102 and fully spirally winding a lane before moving to the next adjacent lane, the transition areas between the lanes is reduced and thus, the helically wound portions are reduced. By reducing the helically wound portions, less compression and more nesting of the plurality of three-dimensional features of the substrate may be achieved. The method may comprise spirally winding a plurality of wraps 114 of the substrate 110 comprising the plurality of three-dimensional features 112 about the core 102 to form a first, spirally wound lane 211.

A majority of, or most of, the three-dimensional features 112 in at least some of, or most of, the wraps 114 of the first, spirally wound lane 211 may be at least partially nested, or fully nested, with a majority of, or most of, the three-dimensional features 112 in an adjacent wrap 114 in the first, spirally wound lane 211. The method may comprise helically winding (shown in dash in FIG. 14 and indicated by lines 114' in FIG. 15) at least ⅕ wrap 114' to at most 6 wraps 114', at least ⅕ wrap 114' to at most 5 wraps 114', at least ⅕ wrap 114' to at most 4 wraps 114', at least ⅕ wrap 114' to at most 3 wraps, at least ⅕ wrap 114' to at most 2 wraps 114', or at least ¼ wrap 114' to at most 3 wraps 114', or at least ½ wrap 114' to at most 2 wraps 114', or about 1 wrap 114', of the substrate 110 about the core 102 to transition to a second lane 212. The helically winding steps in this method will refer to these wrap ranges specified above, although not specified again below in this method for brevity. The method may comprise spirally winding a plurality of wraps 114 of the substrate 110 about the core 102 to form the second, spirally wound lane 212. A majority of, or most of, the three-dimensional features 112 in at least some of, or most of, the wraps 114 of the second lane 212 may be at least partially nested, or fully nested, with a majority of, or most of, the three-dimensional features 112 in an adjacent wrap 114 of the second, spirally wound lane 212. The method may comprise helically winding at least a ⅕ wrap 114' to at most 2 wraps 114' of the substrate 110 about the core 102 to transition to a third lane 213. The method may comprise spirally winding a plurality of wraps 114 of the substrate 110 about the core 102 to form the third, spirally wound lane 213. A majority of the three-dimensional features 112 in at least some of, or most of, the wraps 114 of the third, spirally wound lane 213 may be at least partially nested, or fully nested, with a majority of, or most of, the three-dimensional features 112 in an adjacent wrap 114 of the third, spirally wound lane 213. The method may further comprise applying less than about 10%, less than about 8%, less than about 5%, less than about 3%, less than about 2%, less than about 1%, or about 1% MD strain or tensioning on the substrate 110 during the spirally and helically winding steps. The MD strain or tensioning may be applied by having a speed differential between the substrate being fed to toward the core and the speed that the core is rotated to wind the substrate. The speed of rotation of the core may vary (e.g., slow down) as the spool gains diameter.

The method may further comprise winding more than three lanes, such as by helically winding at least a ⅕ wrap 114' to at most 2 wraps 114' of the substrate 110 about the core 102 to transition to a fourth lane 214 and spirally winding a plurality of wraps 114 of the substrate 110 about the core 102 to form the fourth, spirally wound lane 214. A majority of, or most of, the three-dimensional features 112 in at least some of, or most of, the wraps of the fourth, spirally wound lane 214 may be least partially nested, or fully nested, with a majority of, or most of, the three-dimensional features in an adjacent wrap 114 of the fourth, spirally wound lane 214. The method may further comprise helically winding at least a ⅕ wrap 114' to at most 2 wraps 114' of the substrate 110 about the core 102 to transition to a fifth lane 215. The position of the fifth lane 215 is illustrated in FIGS. 14 and 15, but the fifth lane 215 has not yet been wound. The method may comprise spirally winding a plurality of wraps 114 of the substrate 110 about the core 102 to form the fifth, spirally wound lane 215 (although not illustrated). A majority of, or most of, the three-dimensional features in at least some of, or most of, the wraps 114 of the fifth, spirally wound lane 215 may be at least partially nested, or fully nested, with a majority of, or most of, the three-dimensional features in an adjacent wrap of the fifth, spirally wound lane 215.

In the method described above, the various lanes may be fully wound in order from the first lane 211 to the fifth lane 215 (or more lanes) from a position proximate to the first end 121 to a position proximate to the second end 122 or from the fifth lane 215 (or more lanes) to the first lane 211 from a position proximate to the second end 122 to a position proximate to the first end 121. In this method, the spool 100 may be fully wound as the substrate 110 is moved from the first lane 211 proximate to the first end 121 toward the fifth lane 215 (or more lanes) proximate to the second end 122 or from the fifth lane 215 (or more lanes) proximate to the second end 122 to the first lane 211 proximate to the first end 121. Winding the spool only in one direction and fully spirally winding a lane prior to winding a next adjacent lane reduces the transition areas between the various spirally wound lanes, thereby reducing the amount of the substrate that is helically wound and the amount of three-dimensional features that are compressed and/or not at least partially nested. In some instances, the spool may be wound from the first end 121 to the second end 122 and at least partially back to, or fully back to, the first end 121 to create a fully wound spool or vice versa.

Helically winding (without spiral winding) for substrates comprising a plurality of three-dimensional features is typically not desired in that the three-dimensional features either do not nest, or do not nest as well, as the three-dimensional features nest in adjacent wraps of spirally wound portions. Helically winding the substrate can lead to compression of three-dimensional features. As such, there is a strong desire to reduce the % of helically winding in a spool when the substrate being wound comprises a plurality of three-dimensional features. The winding methods presented above (with reference to FIGS. 14 and 15) accomplish this benefit and have less than about 10%, less than about 8%, less than about 5%, less than about 3%, less than about 2%, less than about 1%, or less than about 0.5% of helically wound portions in the spool once the spool is fully wound. The % of helically wound portions may vary depending on the numbers of lanes desired in a particular spool.

In the method described above, the first lane 211 may be fully spirally wound prior to transitioning to (helically winding) and spirally winding the second lane 212. The second lane 212 may be fully spirally wound prior to transitioning to (helically winding) and spirally winding the third lane 213. The third lane 213 may be fully spirally wound prior to transitioning to (helically winding) and spirally winding the fourth lane 214. The fourth lane 214 may be fully spirally wound prior to transitioning to (helically winding) and spirally winding the fifth lane 215 and so forth to however many lanes are planned for a particular spool.

As can be seen in FIGS. 14 and 15, the first lane 211 is positioned adjacent to the second lane 212, the second lane 212 is positioned adjacent to the third lane 213, the third lane 213 is positioned adjacent to the fourth lane 214, and the fourth lane 214 is positioned adjacent to the fifth lane 215.

Figure 16:
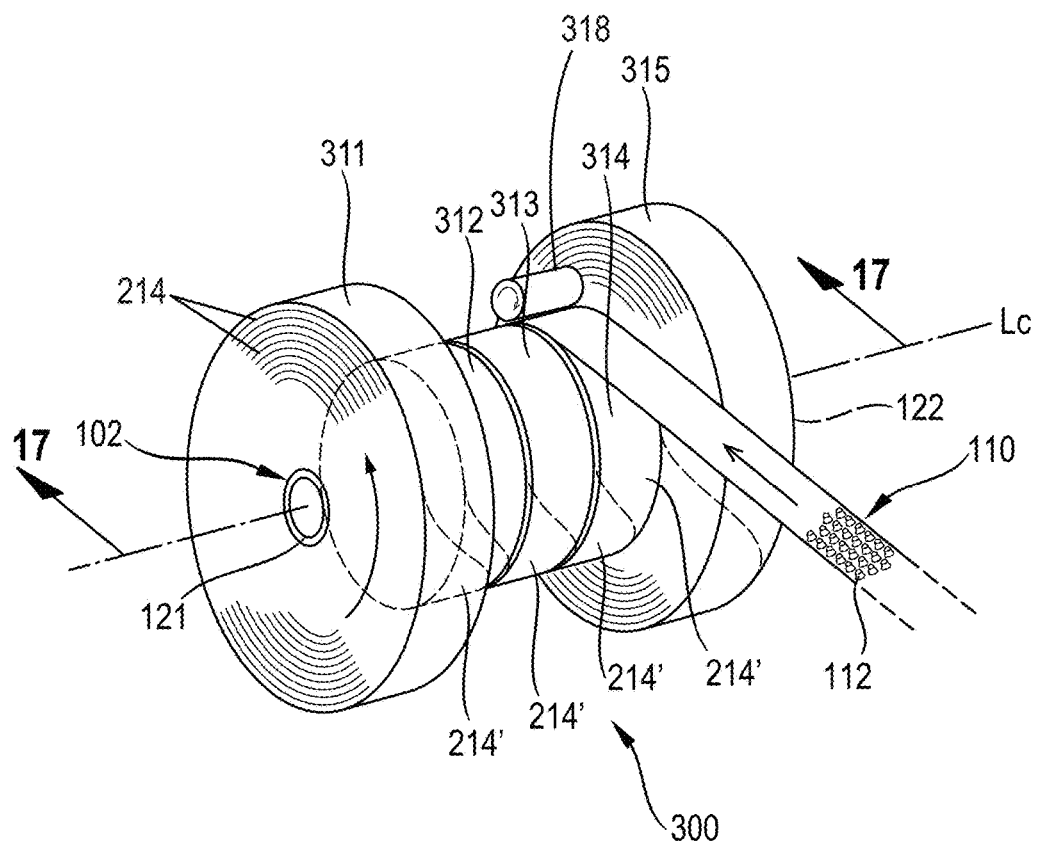
FIG. 16 is a perspective view of a spool being wound in accordance with the methods of the present disclosure.
Figure 17:
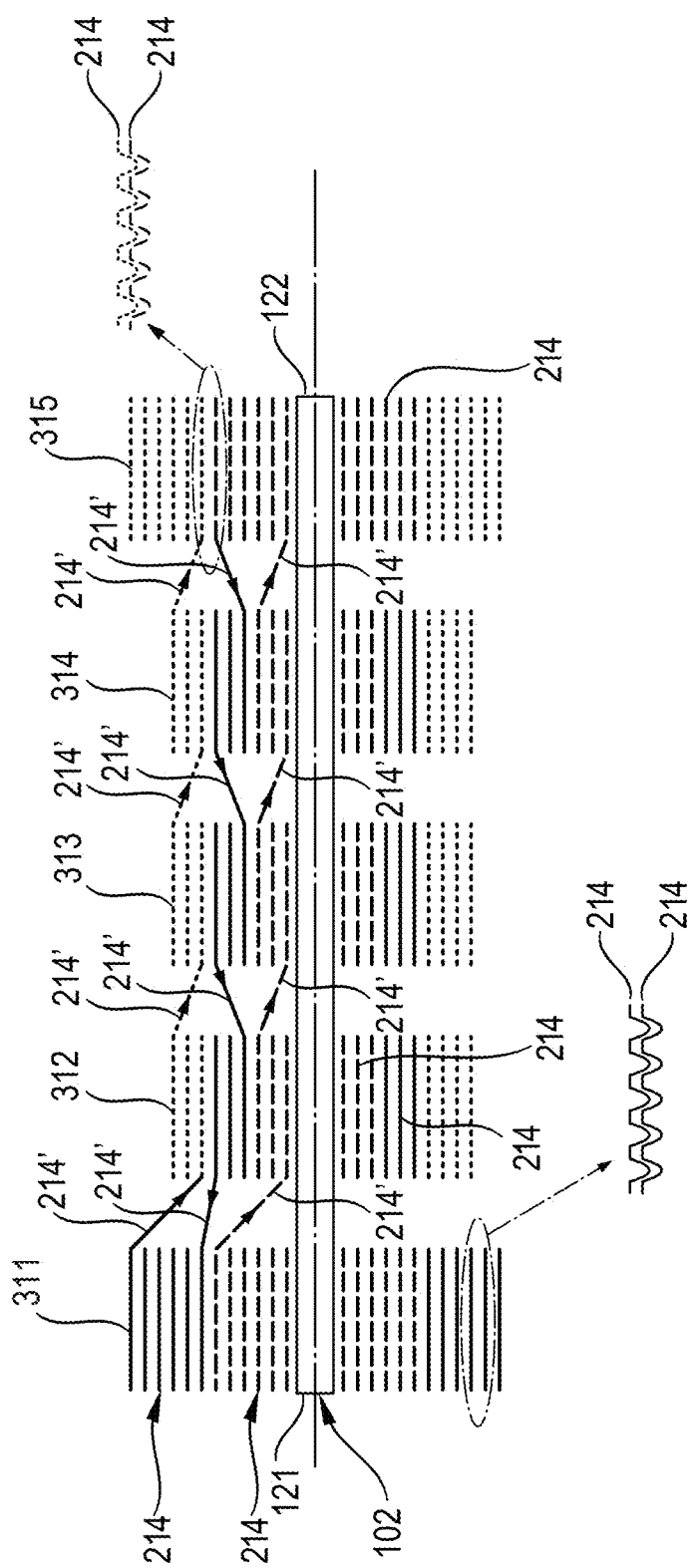
FIG. 17 is a schematic cross-sectional view of the spool taken about line 17-17 of FIG. 16 in accordance with the methods of the present disclosure.

FIGS. 16 and 17 illustrate an example partially wound spool 300 that is being wound by a method of the present disclosure. The partially wound spool 300 comprises a core 102 that may be the same as discussed above. The substrate 110 may also be the same as discussed above. In the methods of winding a substrate 100 comprising a plurality of three-dimensional features 112 illustrated as examples in FIGS. 16 and 17, a step winding process may be used. Essentially, a first number of wraps may be spirally wound on a first lane and a last lane and a second number of wraps may be spirally wound on the lanes intermediate the first and last lanes. The first number of spirally wound wraps may be greater than the second number of spirally wound wraps. As an example, the first number of spirally wound wraps may be 19 and the second number of spirally wound wraps may be 8.2. As another example, the first number of spirally wound wraps may be 9.5 and the second number of spirally wound wraps may be 4.1. As yet another example, the first number of spirally wound wraps may be 60 and the second number of spirally wound wraps may be 30. Many other suitable numbers of the first number of spirally wound wraps and the second number of spirally wound wraps are also within the scope of the present disclosure depending at least upon the substrate being wound and the desired spool characteristics. After the first number of wraps is wound onto, for example, a first lane 311, helical winding may begin to transition to winding a second lane 312. Likewise, after the second number of wraps is wound onto, for example, the second lane 312, helical winding may begin to transition to winding a third lane 313, as so forth.

The method of winding the substrate is directed, at least in part, to reducing the amount of transition areas between the various lanes of the spool 300 to provide a spool 300 with a substrate 110 that is better nested and has less compression of the three-dimensional features 112. The transition areas are equated to the helically wound portions.

The spool 300 may be fully wound from the first end 121 to the second end 122 and then back to the first end 122, or at least partially back to the first end 122. This may be done one time or multiple times depending on the desired diameter of the finished spool. By spirally winding a majority of the substrate in the various lanes, compared to all helical winding as in the related art, the transition areas between the lanes is reduced and thus, the helically wound portions are reduced significantly. By reducing the helically wound portions, less compression and more nesting of the three-dimensional features of the substrate is achieved. The method may comprise spirally winding a plurality of wraps 214 of the substrate 110 comprising a plurality of three-dimensional features 112 about the core 102 to at least partially or partially form a first, spirally wound lane 311. A majority of, or most of, the three-dimensional features 112 in at least some of, or most of, the wraps 214 of the first, spirally wound lane 311 may be at least partially nested, or fully nested, with a majority of, or most of, the three-dimensional features 112 in an adjacent wrap 214 in the first, spirally wound lane 311. The method may comprise helically winding (shown in dash in FIG. 16 and indicated by arrows in FIG. 17) at least ⅕ wrap 214' to at most 5 wraps 214', at least ⅕ wrap 214' to at most 4 wraps 214', at least ⅕ wrap 214' to at most 3 wraps 214', at least ⅕ wrap 214' to at most 2 wraps 214', or at least ¼ wrap 214' to at most 3 wraps 214', or at least ½ wrap 214' to at most 2 wraps 214', or about 1 wrap 214', of the substrate 110 about the core 102 to transition to a second lane 312. The helically winding steps in this method will refer to these wrap ranges herein, although not specified again below in this method for brevity. The method may comprise spirally winding a plurality of wraps 214 of the substrate 110 about the core 102 to partially or at least partially form the second, spirally wound lane 312. A majority of, or most of, the three-dimensional features 112 in at least some of, or most of, the wraps 114 of the second lane 312 may be at least partially nested, or fully nested, with a majority of, or most of, the three-dimensional features 112 in an adjacent wrap 214 of the second, spirally wound lane 312. The method may comprise helically winding at least a ⅕ wrap 214' to at most 2 wraps 214' of the substrate 110 about the core 102 to transition to a third lane 313. The method may comprise spirally winding a plurality of wraps 214 of the substrate 110 about the core 102 to partially or at least partially form the third, spirally wound lane 313. A majority of the three-dimensional features 112 in at least some of, or most of, the wraps 214 of the third, spirally wound lane 313 may be at least partially nested, or fully nested, with a majority of, or most of, the three-dimensional features 112 in an adjacent wrap 214 of the third, spirally wound lane 313. The method may further comprise applying less than about 10%, less than about 8%, less than about 5%, less than about 3%, less than about 2%, less than about 1%, or about 1% MD strain on the substrate during the spirally and helically winding steps.

The method may further comprises winding more than three lanes, such as by helically winding at least a ⅕ wrap 214' to at most 2 wraps 214' of the substrate 110 about the core 102 to transition to a fourth lane 314 and spirally winding a plurality of wraps 214 of the substrate 110 about the core 102 to partially or at least partially form the fourth, spirally wound lane 314. A majority of, or most of, the three-dimensional features 112 in at least some of, or most of, the wraps 214 of the fourth, spirally wound lane 314 may be least partially nested, or fully nested, with a majority of, or most of, the three-dimensional features 112 in an adjacent wrap 214 of the fourth, spirally wound lane 314. The method may further comprise helically winding at least a ⅕ wrap 214' to at most 2 wraps 214' of the substrate 110 about the core 102 to transition to a fifth lane 315. The method may comprise spirally winding a plurality of wraps 214 of the substrate 110 about the core 102 to at least partially or partially form the fifth, spirally wound lane 315. A majority of, or most of, the three-dimensional features 112 in at least some of, or most of, the wraps 214 of the fifth, spirally wound lane 315 may be at least partially nested, or fully nested, with a majority of, or most of, the three-dimensional features 112 in an adjacent wrap of the fifth, spirally wound lane 315.

In the method described above, the various lanes may be wound in order from the first lane 311 to the fifth lane 315 (or more lanes) from the first end 121 towards the second end 122 or from the fifth lane 315 (or more lanes) to the first lane 311 from the second end 122 toward the first end 121. In this method, the spool 100 may be fully wound as the substrate 110 is moved from a position proximate to the first end 121 to a position proximate to the second end 122 or from a position proximate to the second end 122 to a position proximate to the first end 121. Winding the spool only in one direction and fully spirally winding a lane before moving to a next adjacent lane reduces the transition area between the various lanes, thereby reducing the amount of the substrate that is helically wound and the amount of three-dimensional features 112 that are compressed. In some instances, the spool 300 may be wound from a position proximate to the first end 121 to a position proximate to the second end 122 and at least partially back to, or fully back to, the position proximate to the first end 121 to create a fully wound spool or vice versa. In some instances, the spool 300 may only be wound back to the second lane 311 and not all the way to the first lane 311.

As illustrated in FIGS. 16 and 17, the first lane 311 may be positioned adjacent to the second lane 312, the second lane 312 may be positioned adjacent to the third lane 313, the third lane 313 may be positioned adjacent to the fourth lane 313, and the fourth lane 314 may be positioned to the fifth lane 315. Any suitable number of lanes may be wound onto the spool, for example, the number of lanes may be in the range of 3 lanes to 15 lanes, for example.

In the method described above, most or all of the lanes may only be partially wound in one pass of winding the substrate from the position proximate to the first end 121 to the position proximate to the second end 122. For example, the method may comprise only partially spirally winding the first lane 311 prior to transitioning to the second lane 312. In other instances, the method may comprise fully spirally winding the first lane 311 prior to transitioning to the second lane 312. The method may comprise only partially spirally winding the second lane 312 before transitioning to the third lane 313. The method may also comprise only partially spirally winding the third lane 313 prior to transitioning to the fourth lane 314 and only partially spirally winding the fourth lane 314 prior transitioning to the fifth lane 315 (or any other number of lanes).

The method may comprise helically winding at least ⅕ wrap 114' to at most 2 wraps 114' of the substrate 112 about the core 102 to transition to an end lane from one of the central lanes (e.g., lanes 312, 313, 314 or any other number of central lanes) to an end lane positioned proximate to the second end 122. The end lane is represented in FIGS. 16 and 17 as lane 315, but any number of lanes may be present intermediate lanes 311 and 315. Stated another way, the end lane could actually be an eight lane, tenth lane etc.

The method may comprise spirally winding a plurality of wraps 114 of the substrate 110 about the core 102 to form the end lane. A majority of, or most of, the three-dimensional features 112 in at least some of, or most of, the wraps 214 of the end lane may be at least partially nested, or fully nested, with a majority of, or most of, the three-dimensional features 112 in an adjacent wrap 214 of the end lane (e.g., the fifth lane 315). The number of spirally wound wraps 214 in the end lane may be greater than the number of wraps 214 in each of the second lane 312, the third lane 313, and/or the fourth lane 314, and any other lanes intermediate the first lane 311 and the end lane. The end lane may be fully spirally wound or only partially spirally wound before again winding the fourth lane 314 or whatever lane is adjacent to the end lane in a direction back toward the first end 121.

Referring to FIG. 16, one or more nip rolls 318 may be positioned over an outer radial portion of a lane (e.g., fourth lane 314) that is being wound. The nip roll 318 may move between the first end 121 to the second end 121 with the substrate 110 as the spool is being wound. Alternatively, the core 102 may move back and forth (along longitudinal axis, Lc) while the spool is being wound and while the substrate 102 (where it is fed to the core 102) and the nip roll 318 remain stationary. The nip roll 318 may apply a force to the substrate 110 to aid the three-dimensional features 112 of the substrate 110 in nesting with the three dimensional features 112 of a layer of the substrate already wound onto the spool. The nip roll 318 may move radially outwardly as the spool gains diameter.

In the example of FIG. 17, the substrate 110 is wound upon the core from the position proximate to the first end 121 to the position proximate to the second end 122 (i.e., first layer of winding), then from the position proximate to the second end 122 back to the position proximate the first end 121 (i.e., second layer of winding), and then from the position proximate to the first end 121 to the position proximate to the second end 122 (i.e., third layer of winding). The first layer of winding is positioned most proximal to the core 102. The second layer of winding is positioned more distal from the core 102 than the first layer of winding, and the third layer of winding is positioned most distal from the core compared to the second layer of winding. Stated another way, the second layer of winding is positioned more radially outward relative to the core 102 than the first layer of winding and the third layer of winding is positioned more radially outward relative to the core 102 than the second layer of winding. The first layer of winding on the core 102 is indicated by large dashed lines in the wraps 214. The second layer of winding on the first layer of winding is indicated by solid lines in the wraps 214. The third layer of winding on the second layer of winding is indicated by small dashed lines in the wraps 214. Any suitable number of layers of winding between, or at least partially between, the position proximate to the first end 121 and the position proximate to the second end 122 are within the scope of the present disclosure, such as 5, 10, 15, 20, 30, or 50 layers of winding, for example.

Winding from the end lane back towards the first lane 311 will now be discussed in one example instance. This second layer of winding in a direction will occur over the first layer of winding as discussed above. The method may comprise helically winding at least a ⅕ wrap 214' to at most 2 wraps 214' of the substrate 110 about the core 102 in a direction extending from the second end 122 toward the first end 121. The method may comprise spirally winding a second plurality of wraps 214 of the substrate 110 about the core 102 to continue to spirally wind the third lane 313 or any other lane adjacent to the end lane. A majority of, or most of, the three-dimensional 112 features in at least some of, or most of, the second plurality of the wraps 214 of the third lane 313, or any other lane adjacent to the end lane, are at least partially nested, or fully nested, with a majority of, or most of, the three-dimensional features 112 in an adjacent wrap 214 of the second plurality of wraps of the third lane 313 or any other lane adjacent to the end lane. The method may comprise helically winding at least a ⅕ wrap 214' to at most 2 wraps 214' about the core 102 in a direction extending from the second end 122 to the first end 121 to transition to the second lane 312 and spirally winding a second plurality of wraps 214 of the substrate 110 about the core 102 to continue to form the second lane 313. A majority of, or most of, the three-dimensional features 112 in at least some of, or most of, the second plurality of the wraps 214 of the second lane 312 may be at least partially nested, or fully nested, with a majority of, or most of, the three-dimensional features 112 in an adjacent wrap 214 of the second plurality of wraps of the second lane 312. In certain instances, the spool may be fully wound or formed after the second plurality of wraps 214 are spirally wound upon the second lane 312. As such, the steps in the next paragraph may be optional in some circumstances.

The method may comprise optionally helically winding at least a ⅕ wrap 214 to at most 2 wraps 214 about the core 102 in a direction extending from the second end 122 to the first end 121 to transition to the first lane 313. The method may comprise spirally winding a second plurality of wraps 214 of the substrate 110 about the core 102 to continue to spirally wind the first lane 313 (the first lane 313 may or may not be complete at this point depending on the desired size of the finished spool 300). A majority of, or most of, the three-dimensional features 112 in at least some of, or most of, the second plurality of the wraps 214 of the first lane 313 are at least partially nested, or fully nested, with a majority of, or most of, the three-dimensional features 112 in an adjacent wrap 214 of the second plurality of wraps 214 of the first lane 313.

In FIG. 17, the at least partial nesting of various adjacent wraps 214 are illustrated in exploded views.

The present disclosure is also directed, in part, to a method of winding a three-dimensional substrate on a core to create a spool of the three-dimensional substrate. The three-dimensional substrate may comprise a plurality of projections on a first side of the substrate that form a plurality of recesses on a second side of the substrate (i.e., the projections are hollow). The core defines a longitudinal axis and has a first end and second end. The method may comprise spirally winding a plurality of wraps of the three-dimensional substrate about the core to form or at least partially form a first lane. A majority of, or most of, the projections in at least some of, or most of, the wraps of the first lane may be at least partially nested, or fully nested, with a majority of, or most of, the recesses in an adjacent wrap in the first lane. The method may comprise helically winding at least a ⅕ wrap to at most 2 or 3 wraps of the three-dimensional substrate about the core to transition to a second lane. The first lane is positioned more proximal to the first end of the core than the second lane. The method may comprise spirally winding a plurality of wraps of the three-dimensional substrate about the core to form or at least partially form the second lane. A majority of, or most of, the projections in at least some of, or most of, the wraps of the second lane may be at least partially nested, or fully nested, with a majority of, or most of, the recesses in an adjacent wrap of the second lane. The method may comprise helically winding at least a ⅕ wrap to at most 2 or 3 wraps of the three-dimensional substrate about the core to transition to a third lane. The third lane is positioned more proximal to the second end than the second lane. The method may comprise spirally winding a plurality of wraps of the three-dimensional substrate about the core to form or at least partially form the third lane. A majority of, or most of, the projections in at least some of, or most of, the wraps of the third lane are at least partially nested, or fully nested, with a majority of, or most of, the recesses in an adjacent wrap of the third lane. The method set forth in this paragraph may be used in conjunction with other suitable method steps specified herein as will be recognized by those of skill in the art.

The present disclosure is also directed, in part, to a method of winding a three-dimensional substrate on a core to create a spool of the three-dimensional substrate. The three-dimensional substrate may comprise a plurality of projections on a first side of the substrate that form a plurality of recesses on a second side of the substrate (i.e., the projections are hollow). The core defines a longitudinal axis and has a first end and second end. The method may comprise spirally winding a plurality of wraps of the three-dimensional substrate about the core to form or at least partially form a first lane. A majority of, or most of, the projections in at least some of, or most of, the wraps of the first lane are at least partially nested, or fully nested, with a majority of, or most of, the recesses in an adjacent wrap in the first lane. The method may comprise helically winding at least a ⅕ wrap to at most 2 or 3 wraps of the three-dimensional substrate about the core to transition to a second lane. The first lane is positioned more proximal to the first end than the second lane. The method may comprise spirally winding a plurality of wraps of the three-dimensional substrate about the core to form or at least partially form the second lane. A majority of, or most of, the projections in at least some of, or most of, the wraps of the second lane are at least partially nested, or fully nested, with a majority of, or most of, the recesses in an adjacent wrap of the second lane. The method may comprise helically winding at least a ⅕ wrap to at most 2 or 3 wraps of the three-dimensional substrate about the core to transition to a third lane. The third lane is positioned more proximal to the second end than the second lane. The method may comprise spirally winding a plurality of wraps of the three-dimensional substrate about the core to form or at least partially form the third lane. A majority of, or most of, the projections in at least some of, or most of, the wraps of the third lane are at least partially nested, or fully nested, with a majority of, or most of, the recesses in an adjacent wrap of the third lane. The method set forth in this paragraph may be used in conjunction with other suitable method steps specified herein as will be recognized by those of skill in the art.

Helically winding of substrates comprising a plurality of three-dimensional features is typically not desired in that the three-dimensional features either do not nest, or do not nest as well, as the three-dimensional features nest in adjacent wraps of spirally wound lanes. Helically winding of substrate may lead to compression of the plurality of the three-dimensional features. As such, there is a desire to reduce the % of helically winding in a spool when the substrate being wound comprises a plurality of three-dimensional features. As such, the substrates can be wound without significant compression and distortion of the three-dimensional features and be more consumer appealing in final products. The winding methods presented above (with reference to FIGS. 16 and 17) accomplish this benefit and have less than about 40%, less than about 35%, less than about 30%, less than about 25%, less than about 20%, less than about 18%, about 16%, or in the range of about 5% to about 35% of helically wound portions in the spool once fully wound.

The substrates discussed herein comprising the plurality of three-dimensional features may nest with themselves in various adjacent spirally wound wraps. The three-dimensional features in one spirally wound wrap of the substrate may nest with at least 50%, at least 60%, at least 70%, at least 80%, at least 90%, or at least 95% of the three-dimensional features in another adjacent spirally wound wrap of the substrate. In other instances, three-dimensional features in one spirally wound wrap of the substrate may nest with between about 50% and about 99%, between about 55% and about 95%, between about 60% and about 95%, or between about 65% and about 90% of the three-dimensional features in another adjacent spirally wound wrap, specifically reciting all 0.5% increments within the above-specified ranges and all ranges formed therein or thereby.

Figure 18:
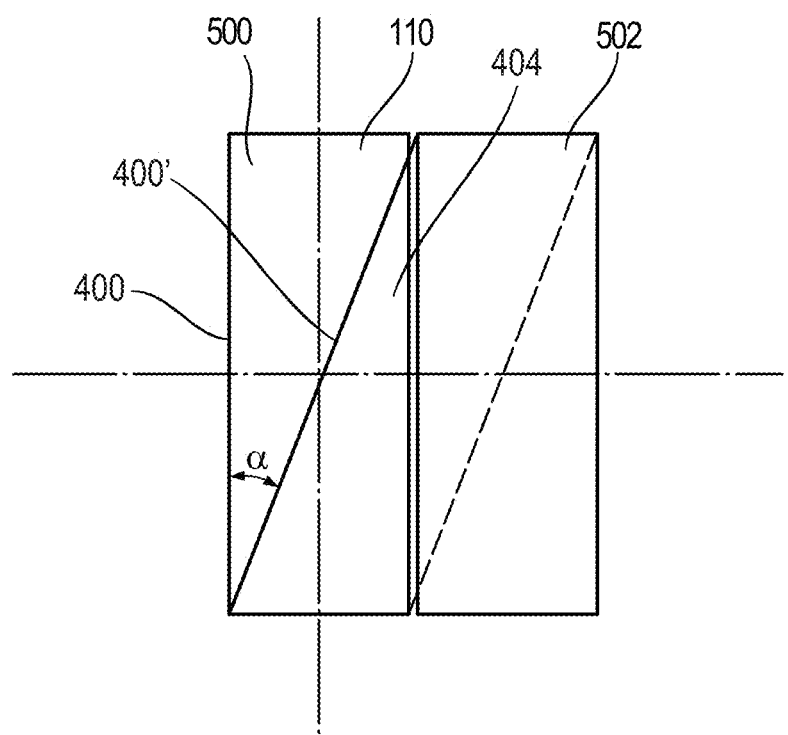
FIG. 18 is a front view of a two spirally wound lanes of a substrate being connected by a helically wound portion in accordance with the methods of the present disclosure.

FIG. 18 illustrates a first spirally wound lane 500 of the substrate 110 and a second adjacent spirally wound lane 502 of the substrate 110. A helically wound portion 404 extends between the first spirally wound lane 500 and the second spirally wound lane 502. The helically wound portions discussed herein may have an angle alpha, $\alpha$, measured between a side edge 400 of the lane first lane and a side edge 400' of the substrate 100 when entering the first helically wound wrap (or partial wrap) 404. The angle alpha, $\alpha$, may be between about 0.3 degrees and about 60 degrees, about 0.3 degrees and about 45 degrees, between about 3 degrees and about 40 degrees, between about 3 degrees and about 35 degrees, or between about 5 degrees and about 30 degrees, specifically reciting all 0.1 degrees increments within the specified ranges and all ranges formed therein or thereby. The angle alpha, $\alpha$, may vary as the substrate comprising the plurality of three-dimensional features is wound from the core 102 to an outer radial wrap of the spool. The angle alpha, $\alpha$, may also be constant from the core 102 to an outer radial warp of the spool.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of winding a substrate comprising a nonwoven on a core to create a spool of the substrate, wherein the substrate comprises a plurality of three-dimensional features, and wherein the core defines a longitudinal axis and has a first end and second end, the method comprising:
    spirally winding a plurality of wraps of the substrate about the core to at least partially form a first lane, wherein a majority of the three-dimensional features in at least some of the wraps of the first lane are at least partially nested with a majority of the three-dimensional features in an adjacent wrap in the first lane;
    helically winding at least a ⅕ wrap to at most 2 wraps of the substrate about the core to transition to a second lane;
    spirally winding a plurality of wraps of the substrate about the core to at least partially form the second lane, wherein a majority of the three-dimensional features in at least some of the wraps of the second lane are at least partially nested with a majority of the three-dimensional features in an adjacent wrap of the second lane;
    helically winding at least a ⅕ wrap to at most 2 wraps of the substrate about the core to transition to a third lane;
    spirally winding a plurality of wraps of the substrate about the core to at least partially form the third lane, wherein a majority of the three-dimensional features in at least some of the wraps of the third lane are at least partially nested with a majority of the three-dimensional features in an adjacent wrap of the third lane; and
    applying less than 10% machine direction strain on the substrate during the spirally and helically winding steps.

2. The method of claim 1, comprising:
    helically winding at least a ⅕ wrap to at most 2 wraps of the substrate about the core to transition to a fourth lane; and
    spirally winding a plurality of wraps of the substrate about the core to at least partially form the fourth lane, wherein a majority of the three-dimensional features in at least some of the wraps of the fourth lane are at least partially nested with a majority of the three-dimensional features in an adjacent wrap of the fourth lane.

3. The method of claim 2, comprising:
    helically winding at least a ⅕ wrap to at most 2 wraps of the substrate about the core to transition to a fifth lane; and
    spirally winding a plurality of wraps of the substrate about the core to at least partially form the fifth lane, wherein a majority of the three-dimensional features in at least some of the wraps of the fifth lane are at least partially nested with a majority of the three-dimensional features in an adjacent wrap of the fifth lane.

4. The method of claim 1, comprising fully spirally winding the first lane prior to spirally winding the second lane.

5. The method of claim 4, comprising fully spirally winding the second lane prior to spirally winding the third lane.

6. The method claim 5, comprising:
    fully winding the spool in a first direction extending from the first end to the second end; or
    fully winding the spool in a second direction extending from the second end to the first end.

7. The method of claim 1, wherein the first lane is positioned adjacent to the second lane, and wherein the second lane is positioned adjacent to the third lane.

8. The method of claim 1, comprising only partially spirally winding the first lane prior to transitioning to the second lane.

9. The method of claim 8, comprising only partially spirally winding the second lane prior to transitioning to the third lane.

10. The method of claim 9, wherein the first lane, the second lane, and the third lane extend in a first direction extending between the first end and the second end.

11. The method of claim 1, comprising helically winding at least a ⅕ wrap to at most 2 wraps of the substrate about the core to transition to an end lane positioned proximate to the second end.

12. The method of claim 11, comprising spirally winding a plurality of wraps of the substrate about the core to form the end lane, wherein a majority of the three-dimensional features in at least some of the wraps of the end lane are at least partially nested with a majority of the three-dimensional features in an adjacent wrap of the end lane.

13. The method of claim 12, comprising spirally winding a greater number of wraps in the end lane than in the third lane.

14. The method of claim 13, comprising helically winding at least a ⅕ wrap to at most 2 wraps of the substrate about the core in a direction extending from the second end toward the first end.

15. The method of claim 14, comprising spirally winding a second plurality of wraps of the substrate about the core to continue to spirally wind the third lane, wherein a majority of the three-dimensional features in at least some of the second plurality of the wraps of the third lane are at least partially nested with a majority of the three-dimensional features in an adjacent wrap of the second plurality of wraps of the third lane.

16. The method of claim 15, comprising:
    helically winding at least a ⅕ wrap to at most 2 wraps about the core in a direction extending from the second end to the first end to transition to the second lane; and
    spirally winding a second plurality of wraps of the substrate about the core to continue to form the second lane, wherein a majority of the three-dimensional features in at least some of the second plurality of the wraps of the second lane are at least partially nested with a majority of the three-dimensional features in an adjacent wrap of the second plurality of wraps of the second lane.

17. The method of claim 16, comprising:
helically winding at least a ⅕ wrap to at most 2 wraps about the core in a direction extending from the second end to the first end to transition to the first lane; and
spirally winding a second plurality of wraps of the substrate about the core to continue to spirally wind the first lane, wherein a majority of the three-dimensional features in at least some of the second plurality of the wraps of the first lane are at least partially nested with a majority of the three-dimensional features in an adjacent wrap of the second plurality of wraps of the first lane.

18. The method of claim 1, wherein the plurality of three-dimensional features comprise a plurality of projections on a first side of the substrate that form a plurality of recesses on a second side of the substrate.

19. The method of claim 18, wherein the plurality of three-dimensional features comprise a plurality of second recesses on a first side of the substrate and a plurality of second projections on the second side of the substrate.

20. The method of claim 1, wherein the substrate comprises apertures.

21. The method of claim 1, comprising applying less than 5% MD strain on the substrate during the spirally and helically winding steps.

22. A method of winding a three-dimensional substrate on a core to create a spool of the three-dimensional substrate, wherein the three-dimensional substrate comprises a plurality of projections on a first side of the substrate that form a plurality of recesses on a second side of the substrate, and wherein the core defines a longitudinal axis and has a first end and second end, the method comprising:
spirally winding a plurality of wraps of the three-dimensional substrate about the core to at least partially form a first lane, wherein a majority of the projections in at least some of the wraps of the first lane are at least partially nested with a majority of the recesses in an adjacent wrap in the first lane;
helically winding at least a ⅕ wrap to at most 2 wraps of the three-dimensional substrate about the core to transition to a second lane, wherein the first lane is positioned more proximal to the first end than the second lane;
spirally winding a plurality of wraps of the three-dimensional substrate about the core to at least partially form the second lane, wherein a majority of the projections in at least some of the wraps of the second lane are at least partially nested with a majority of the recesses in an adjacent wrap of the second lane;
helically winding at least a ⅕ wrap to at most 2 wraps of the three-dimensional substrate about the core to transition to a third lane, wherein the third lane is positioned more proximal to the second end than the second lane;
spirally winding a plurality of wraps of the three-dimensional substrate about the core to at least partially form the third lane, wherein a majority of the projections in at least some of the wraps of the third lane are at least partially nested with a majority of the recesses in an adjacent wrap of the third lane; and applying less than 10% machine direction strain on the substrate during the spirally and helically winding steps.

23. A method of winding a three-dimensional substrate on a core to create a spool of the three-dimensional substrate, wherein the three-dimensional substrate comprises a plurality of projections on a first side of the substrate that form a plurality of recesses on a second side of the substrate, and wherein the core defines a longitudinal axis and has a first end and second end, the method comprising:
spirally winding a plurality of wraps of the three-dimensional substrate about the core to at least partially form a first lane, wherein a majority of the projections in at least some of the wraps of the first lane are at least partially nested with a majority of the recesses in an adjacent wrap in the first lane;
helically winding at least a ⅕ wrap to at most 2 wraps of the three-dimensional substrate about the core to transition to a second lane, wherein the first lane is positioned more proximal to the first end than the second lane;
spirally winding a plurality of wraps of the three-dimensional substrate about the core to at least partially form the second lane, wherein a majority of the projections in at least some of the wraps of the second lane are at least partially nested with a majority of the recesses in an adjacent wrap of the second lane;
helically winding at least a ⅕ wrap to at most 2 wraps of the three-dimensional substrate about the core to transition to a third lane, wherein the third lane is positioned more proximal to the second end than the second lane;
spirally winding a plurality of wraps of the three-dimensional substrate about the core to at least partially form the third lane, wherein a majority of the projections in at least some of the wraps of the third lane are at least partially nested with a majority of the recesses in an adjacent wrap of the third lane;
wherein the helically winding comprises less than 35% of the spool; and applying less than 10% machine direction strain on the substrate during the spirally and helically winding steps.

* * * * *